United States Patent [19]

Afromowitz

[11] Patent Number: 5,009,102
[45] Date of Patent: Apr. 23, 1991

[54] METHOD OF MONITORING SOLIDIFICATION OF A LIQUID COMPOSITION

[75] Inventor: Martin A. Afromowitz, Seattle, Wash.

[73] Assignee: Board of Regents of the University of Washington, Seattle, Wash.

[21] Appl. No.: 444,754

[22] Filed: Dec. 1, 1989

Related U.S. Application Data

[62] Division of Ser. No. 147,234, Jan. 22, 1988, Pat. No. 4,904,080.

[51] Int. Cl.$^5$ .............................................. G01N 29/20
[52] U.S. Cl. .......................................... 73/590; 73/599
[58] Field of Search .......................... 73/590, 599, 644; 374/53, 117

[56] References Cited

U.S. PATENT DOCUMENTS

| 4,412,451 | 11/1983 | Uusitalo et al. | 73/599 |
| 4,590,803 | 5/1986 | Harrold | 73/590 |
| 4,798,954 | 1/1989 | Stevenson | 250/341 |
| 4,867,167 | 9/1989 | Magnin | 73/599 |

OTHER PUBLICATIONS

Harrold et al., "Non-Destructive Evaluation of the Curing of Resin and Prepreg Using an Acoustic Waveguide Sensor," From: *Review of Progress in Quantitative Nondestructive Evaluation*, vol. 6B, pp. 1277–1285, Edited by Donald O. Thompson and Dale E. Chimenti (Plenum Publishing Corporation, 1987).

Lindrose, A. M., "Ultrasonic Wave and Moduli Changes in a Curing Epoxy Resin," *Experimental Mechanics*, pp. 227–232, Jun. 1978.

Harrold et al., "Material Cure and Internal Stresses Monitored Via Embedded Acoustic Waveguides," Reprinted from: *Proceedings of ICTTE 86 Technology Shaping Our Future*, 1986 International Congress on Technology and Technology Exchange, Pittsburgh, Pa., Oct. 6–8, 1986.

Rokhlin et al., "Real-Time Study of Frequency Dependence of Attenuation and Velocity of Ultrasonic Waves During the Curing Reaction of Epoxy Resin," *J. Acoust. Soc. Am.*, vol. 79(6), pp. 1786–1793, Jun. 1986.

Primary Examiner—Hezron E. Williams
Assistant Examiner—Rose M. Finley
Attorney, Agent, or Firm—Christensen, O'Connor, Johnson & Kindness

[57] ABSTRACT

Reference materials of differing indices of refraction or acoustic impedances are incorporated into liquid compositions to monitor the solidification process of these liquid compositions. Light or acoustic waves are used to indirectly measure the difference between the index of refraction or acoustic impedance of the solidfying composition and the reference material. The method provides an accurate in situ indication of the completion of the solidification process as well as a monitor of the degree of solidification during the solidification process.

8 Claims, 2 Drawing Sheets

METHOD OF MONITORING SOLIDIFICATION OF A LIQUID COMPOSITION

This is a divisional of the prior application Ser. No. 07/147,234 filed Jan. 22, 1988, now U.S. Pat. No. 4,904,080, issued Feb. 27, 1990. The benefit of the filing date of which are hereby claimed under 35 U.S.C. § 120.

BACKGROUND OF THE INVENTION

The present invention relates to a method for monitoring the solidification of a liquid composition as it passes from a liquid phase to a solid phase.

The change of a liquid composition from a liquid phase to a solid phase occurs in many chemical reactions such as the polymerization of liquid monomers to a solid polymer, curing of thermoset resins such as epoxy resins or polyimides, and cross-linking of single chain polymers. Monitoring the degree of solidification, i.e., completion, of these exemplary types of reactions is advantageous to ensure that the solid product has the desired chemical and physical properties associated with the completion of the reaction, as well as to minimize the energy and time costs associated with maintaining the process conditions past the point of completion.

For example, precision curing conditions are required in the production of cured thermosettable materials and composite materials containing these cured thermosettable materials that are finding increasing use in a variety of advance materials applications. The precision of the curing process is important because the ultimate mechanical properties of these materials depends primarily on completely and uniformly curing these materials. For instance, in a large molded structure of a thermoset resin, the degree of cure may vary from place to place within the structure due to the lack of homogeneity of the starting materials, the exothermic nature of the curing reaction, the thermodiffusivity of the material, and the thermal characteristics of the curing oven or the geometry of the mold.

A common method for characterizing the degree of cure of thermosettable materials involves the measurement of the glass transition temperature ($T_g$) by one of a number of different techniques. Examples of these techniques include differential scanning calorimetry and thermoexpansion measurements. The equipment associated with these bulk methods are hard to adapt to local in situ measurements, that are necessary to accurately monitor the curing process throughout a large body.

A technique known as dielectric spectroscopy has undergone development resulting in a method for the in situ measurement of the local dielectric properties of curing materials. A frequency range of 0.005 to 10,000 Hz is used to monitor changes in the dielectric loss factor that have been shown to correlate with different stages of the curing process. Another technique recognizes that the intensity and wavelength of fluorescence of certain molecules are dependent upon the viscosity of the environment surrounding the molecules. Because the viscosity of a composition changes with the degree of cure, it is possible to monitor the degree of cure by indirectly monitoring the change in the viscosity of the thermosettable composition and detecting the resultant effect on the fluorescence of the molecules. In still another technique, the attenuation and phase velocity of ultrasonic waves in thermosettable materials is known to vary during the curing process primarily due to the change in viscosity of the materials. An ultrasonic spectral analysis technique has been used to measure the frequency dependence of the ultrasonic velocity and attenuation during the curing process of a thermosettable composition at a fixed temperature.

The prior techniques show the onset of the curing reaction in thermosettable materials. However, during the curing process, properties of the thermosettable material, such as viscosity, conductivity and glass transition temperature, change drastically at the onset of curing and then saturate at an upper bound as the curing process continues and nears completion. For example, as methylmethacrylate polymerizes and cures, the instantaneous glass transition temperature changes from $-102.8°$ to $70°$ C., and the viscosity rises from about 0.1 to $1 \times 10^{11}$ centipoise. Using a fluorescent probe method, a fluorescent probe molecule added to the methylmethacrylate system exhibits an intensity change from 4 to 75 relative units. Unfortunately, by the time the glass transition temperature has reached $40°$ C., the viscosity has reached only $2 \times 10^4$ centipoise and the fluorescent intensity has already reached 72.5. The final stages of the curing process must be measured by the remaining 2.5 relative units of the fluorescent intensity and therefore the final stages of the curing process are not observable with adequate resolution. The glass transition temperature and dielectric spectroscopy methods of monitoring the curing of thermosettable resin compositions also suffer from similar limitations, in addition, both these methods are not readily adaptable to in situ measurements of large structures, where the monitoring of the solidification process is most important.

SUMMARY OF THE INVENTION

The present invention addresses the inadequacies of the prior methods used for the in situ monitoring of the solidification of a liquid composition, such as thermoset resins. The invention provides an accurate monitor of the solidification process that ensures the solid product will have the desired properties associated with the fully and uniformly solidified product. The method relies upon monitoring the difference between the index of refraction or acoustic impedance of the liquid composition and a reference material that are subjected to conditions that cause the liquid composition to solidify. In a preferred embodiment, the solidification process is monitored using an optical or acoustical waveguide that passes through the liquid composition. The waveguide has an index of refraction or an acoustic impedance that is greater than the index of refraction or acoustic impedance of the composition in a liquid state. When the composition is fully-solidified, it has an index of refraction or acoustic impedance that is substantially equal to the index of refraction or acoustic impedance of the waveguide. While the liquid composition containing the optical or acoustic waveguide is subjected to solidifying conditions, light or sound waves are introduced into the portion of the waveguide that passes through the liquid composition. Because several of the transmission characteristics of the waveguide (e.g., critical angle, mode structure and attenuation) are dependent on the difference between the index of refraction or acoustic impedance of the waveguide and the liquid composition, the degree of solidification is monitored by determining at least one transmission characteristic of the waveguide passing through the solidifying composition. For example, when the difference between the index of refraction or the acoustic impedance of the waveguide and the liquid composition is at its greatest, that is, before the liquid begins to solidify, the intensity of the introduced light or sound waves transmitted through the waveguide is at its maximum; however, as the liquid composition solidifies and the difference diminishes, the intensity of the transmitted light or sound waves proportionally decreases because increasing light or sound power is coupled out of the waveguide. Thus, the relative intensity of the light or acoustic energy transmitted through the waveguide provides an indication of the degree of solidification of the composition.

A solidification process may also be monitored by dispersing particles having an index of refraction $n_1$ in the liquid composition having an index of refraction $n_2$. The index of refraction $n_1$ is unequal to the index of refraction $n_2$. The composition in its fully-solidified phase, has an index of refraction $n_3$ that is substantially equal to $n_1$. The difference between the indices of refraction $n_1$ and $n_2$ cause the particles to scatter light that is introduced into the solidifying composition until the solidification process provides a solid product having an index of refraction $n_3$ that is substantially equal to $n_1$; the scattered light is detected and used to determine the degree of solidification of the liquid composition. Similarly, particles having an acoustic impedance $Z_1$ can be dispersed in the liquid composition having an acoustic impedance $Z_2$ different from $Z_1$. The liquid composition in its fully solidified phase has an acoustic impedance $Z_3$ that is substantially equal to $Z_1$. The difference between the acoustic impedances $Z_1$ and $Z_2$ cause acoustic waves introduced into the solidifying composition to be scattered until the solidification process provides a solid product having an acoustic impedance $Z_3$ that is substantially equal to $Z_1$. The scattered acoustic waves are detected and used to determine the degree of solidification of the liquid composition.

In accordance with the present invention, another method of monitoring a solidification process includes providing a transparent ellipsoidal sensor structure having an index of refraction $n_1$ and a first and second focus. A first optical waveguide is terminated at the first focus and a second optical waveguide is terminated at the second focus. The longitudinal axes of the optical waveguides at their termination within the ellipsoidal sensor and the major axis of the ellipsoidal sensor structure are coplanar. In addition, the first and second optical waveguides are preferably arranged so that light may not pass directly from one waveguide to the other, but instead, the light emanating from the end of the first waveguide and reflected from the surface of the ellipsoidal sensor structure would optimally enter and be guided in the second waveguide. The ellipsoidal sensor structure is surrounded by a liquid composition having an index of refraction $n_2$, such that $n_2$ does not equal $n_1$. The solidified liquid composition has an index of refraction $n_3$, such that $n_3$ is substantially equal to $n_1$. Light that is transmitted to the first focus through the first optical waveguide is reflected by the interface between the ellipsoidal sensor structure and the solidifying composition, and refocused by the ellipsoidal interface onto the second focus. The difference between the indices of refraction $n_1$ and $n_2$ cause the light transmitted to the first focus to be reflected by the interface between the ellipsoidal sensor structure and the solidifying composition until the solidification process provides a solid product having an index of refraction $n_3$ that is substantially equal to $n_1$. The light reflected is transmitted away from the second focus by the second optical waveguide. The intensity of light in the second optical waveguide is detected and used to monitor the degree of solidification of the liquid composition.

Other objects, features, and advantages of the present invention will be readily apparent from the following description of certain preferred embodiments thereof, taken in conjunction with the accompanying drawings. It is understood that variations and modifications may be affected without departing from the spirit and scope of the novel concepts of the disclosure.

DETAILED DESCRIPTION OF THE INVENTION

Figure 1:
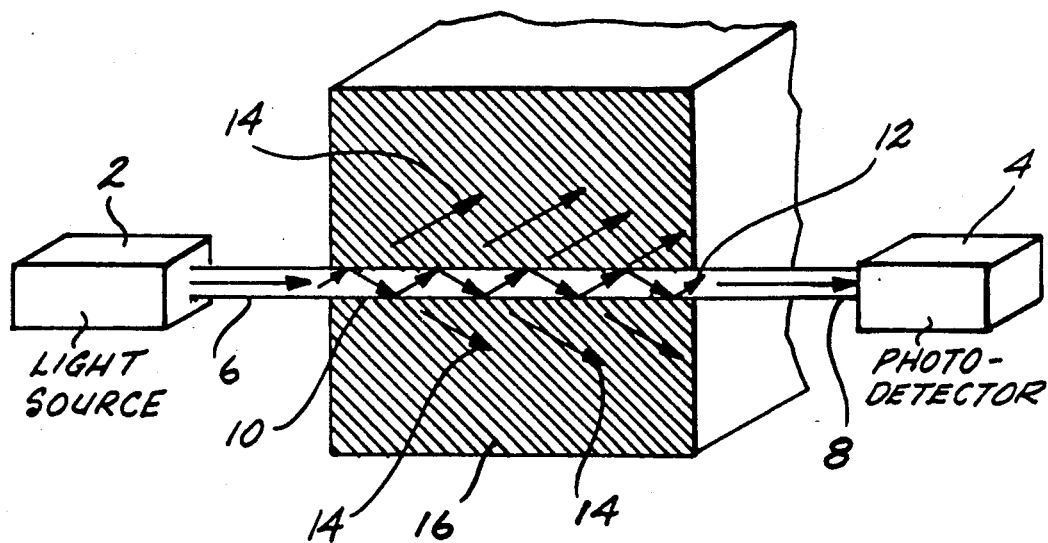
FIG. 1 is a schematic diagram of a first apparatus constructed in accordance with a preferred embodiment of the present invention.

The present invention is generally applicable to any process wherein it is desired to monitor a change of a liquid composition from a liquid phase to a solid phase. Examples of these types of processes include reactions wherein liquid monomers such as styrene, phenol-formaldehyde or phenolics are polymerized to solid polymers, liquid resins are cured to solid resins such as epoxy resins and polyimides and straight chain liquid polymers are cross-linked to solid polymers. Also included are other materials that undergo a physical change, particularly when passing from a liquid phase to a solid phase. These materials include metals, plastics, cement, concrete and the freezing of various liquids. Though not intended to be limited to a particular chemical reaction or family of liquid compositions, the present invention will be described with reference to the particular family of liquid compositions known as thermosettable resins.

Thermosetting resins are well-known and are widely used as matrices for advanced composite materials and structural adhesives. The fabrication of strong composite materials or uniform adhesive joints requires curing the resin material under proper thermal and pressure conditions to an optimal degree. Thermoset resins are generally high polymers that solidify or set irreversibly when heated. This property is usually associated with a cross-linking reaction of the molecular constituents induced by heat or radiation. During the curing reaction, the thermosetting resin transforms from the viscous liquid state to a gel and then vitrifies to the solid glass state. In some instances, it may be necessary to add conventional curing agents such as organic peroxides and the like. Phenolics, alkyls, amino resins, polyesters, epoxides and silicones are usually considered to be thermosetting resins, but the term may also apply to materials where additive induced cross-linking is possible.

An epoxy resin is a specific example of a thermoset resin. The most common epoxy resins are made from epichlorohydrin and bisphenol A, however, aliphatic polyols such as glycerol may be used instead of the aromatic bisphenol A. Epoxy resins of this type have glycidol ether structures in the terminal positions, many hydroxyl groups, and cure readily with amines. Another type of epoxy resin is made from polyolefins oxidized with acetic acid. These epoxy resins have more epoxide groups within the molecule as well as in terminal positions, and can be cured with anhydrides at high temperatures. The epoxy resins form a tight cross-linked polymer network, and are characterized by toughness, good adhesion, corrosion resistance, chemical resistance, and good dielectric properties. Many modifications of both types of epoxy resins are available commercially.

Another example of thermoset resins include the polyimides. Polyimides are derived from a pyromellitic dianhydride and an aromatic diamine. The polyimides exhibit excellent frictional characteristics, good wear resistance at high temperatures, and resistance to radiation and combustion. The thermosettable polyimides have found widespread application in high-temperature coatings, laminates and composites for aerospace vehicles, and as adhesives.

In the present discussion, the term "liquid composition" generally includes the thermoset resin in an uncured state. The term "solidifying composition" generally includes the thermosetting resin that is subjected to curing conditions and is passing from the liquid phase to the solid phase. The term "solid composition" generally includes the thermoset resin in a cured solid form. When referring to other liquid compositions, it should be understood that the term "uncured composition" can be used interchangeably in the present specification and claims with the term "liquid composition." Likewise, the term "curing composition" can be used interchangeably with the term "solidifying composition" and the term "cured composition" can be used interchangeably with the term "solid composition." The term "solid product" or "cured product" refers to the product of the solidification process that is being monitored.

The method of the present invention, as it applies to thermosetting resins, relies upon monitoring the difference between the index of refraction or acoustic impedance of the solidifying composition and the index of refraction or acoustic impedance of a reference material during the curing, i.e., solidifying process in the resins. The method incorporates a reference material having a known index of refraction or acoustic impedance into the uncured composition and monitors the difference between the indices of refraction or acoustic impedances of the reference material and the curing composition by detecting the waveguiding, reflecting, or scattering effects on light or sound waves passing through the curing composition or the incorporated reference material. The reference material is preferably chosen so that its index of refraction or acoustic impedance is substantially equal to the index of refraction or acoustic impedance of the cured product. The term "substantially equal to" as used herein means that the difference between the index of refraction or the acoustic impedance of the reference material and the cured product is such that light or sound waves passing from the cured product, having a first index of refraction or acoustic impedance, to the reference material, having a second index of refraction or acoustic impedance are virtually unaffected by the difference in the indices of refraction or acoustic impedances. The index of refraction or acoustic impedance of the reference material provides the baseline or reference standard to which the index of refraction or acoustic impedance of the curing composition or cured product is indirectly compared. A direct measurement of the indices of refraction or acoustic impedances is not made, but rather the difference between the index of refraction or the acoustic impedance of the curing composition or cured product and the reference material is measured by monitoring the reflection or scattering of light resulting from the differing indices of refraction or the reflection or scattering of acoustic waves due to differences between the acoustic impedances or the optical or acoustical waveguiding properties of certain structures fabricated preferably from the reference material and incorporated in the curing composition.

In accordance with a preferred embodiment of the present invention, an optical or acoustical waveguide is passed through the uncured composition and used to monitor the degree of cure in the curing composition. The optical waveguides useful in the present invention are generally fibers of circular cross-section having a waveguiding composition at least on the periphery of the waveguide. These fibers range in diameter from about 10 to about 1000 microns and may be made from materials such as glass, plastic and the like. The optical waveguide must have a lightguiding region when surrounded by the uncured or curing composition. In addition, the transmission characteristics of this lightguiding region must be sensitive to changes in the index of refraction of the curing composition. Therefore, one may use a fiber of uniform composition having an index of refraction $n_1$ greater than the index of refraction $n_2$ of the uncured composition. The optical waveguide is preferably an optical fiber made of the uncured composition in a cured form. This ensures that the optical waveguide has an index of refraction $n_1$, that is substantially equal to the index of refraction $n_3$, of the cured product and greater than the index of refraction $n_2$, of the uncured composition. The use of optical waveguides of the cured composition is also desirable because the index of refraction of the waveguide is affected by the process conditions, for example, pressure and temperature, in the same manner as the index of refraction of the cured product. Therefore, any error in monitoring the curing process attributable to the differing effect of the process conditions on the index of refraction of the waveguide and the cured product is eliminated by using waveguides prepared from the cured composition.

Light is supplied to the optical waveguide at a first end from a conventional light source. Examples of such conventional light sources include a laser, a light emitting diode and the like. The light source supplies the light to the optical waveguide that will be preferably detected at the second end of the waveguide and used to determine the transmission characteristics of the waveguide such as the critical angle, mode structure or the attenuation of the waveguide. Any wavelength of light waves that the waveguide will transmit may be used, although the wavelength of the light should be such that its attenuation in the waveguide surrounded by the curing composition is not excessive, preferably, the wavelength is about 400 to about 1500 nanometers.

In order for an optical waveguide to effectively transmit light, the index of refraction $n_2$, of the medium surrounding the optical waveguide must be less than the index of refraction $n_1$, of the optical waveguide so that a light ray traveling within the optical waveguide and striking the surface of the waveguide at an angle of incidence, measured with respect to the direction perpendicular to the surface of the waveguide, greater than the critical angle, $\theta_C$, given by $\sin \theta_C = n_2/n_1$, will be guided by total internal reflection. As the indices of refraction approach each other, the critical angle $\theta_C$ increases, therefore less light can be guided. Any light ray traveling in the waveguide and striking the surface of the waveguide at an angle of incidence less than $\theta_C$ escapes the optical waveguide. Therefore, in the context of the present invention, because of the differences in the indices of refraction between the optical waveguide and the curing composition at the beginning of the curing process, a certain fraction of the light introduced into the optical waveguide is internally reflected and transmitted by the optical waveguide through the length of the waveguide which is surrounded by the curing composition. As the degree of cure increases, and the index of refraction $n_2$, of the curing composition increases and approaches the index of refraction $n_1$, of the optical waveguide, the transmission characteristics of the waveguide will change, e.g., the intensity of light internally reflected and transmitted by the optical waveguide through the curing composition diminishes.

The intensity of light transmitted by the optical waveguide and other transmission characteristics of the waveguide such as the critical angle and mode structure can be determined by a photodetector positioned at the second end of the optical waveguide. Conventional photodetectors commercially available can be employed. Optionally, it is possible to reflect the lightwave back into the second end of the waveguide by placing an optically mismatched material on the second end of the waveguide. In this instance, the light source and the photodetector will be coupled to the first end of the optical waveguide in a manner that allows the light source to provide the light to the waveguide and allows the detector to detect the reflected light. The transmission characteristics of the optical waveguide surrounded by the curing composition can be compared to predetermined reference standards for a given light source to monitor the degree of cure during the curing process. These reference standards for a given light source provide a relationship between the waveguiding characteristics of the optical waveguide and the degree of cure during the curing process. The relationships can be established by simultaneously monitoring the degree of cure by an independent means such as Differential Scanning Calorimetry or Differential Thermal Analysis and relating this information to the waveguide characteristics of the optical waveguide during the curing process.

When the optical waveguide is employed, it is possible to determine the completion of the curing of the resin without referring to reference standards. Because the optical waveguide has an index of refraction $n_1$, substantially equal to the index of refraction $n_3$, of the cured product, and is preferably of the same composition as the cured product, when the resin is completely cured, the indices of refraction are substantially equal, and substantially all of the light introduced into the optical waveguide will escape from the optical waveguide into the cured product. In other words, the critical angle will be substantially 90 degrees when the curing of the resin is complete and the attenuation of the waveguide as detected by the photodetector will be at a maximum as evidenced by a substantial absence of any detectable intensity of light being transmitted by the optical waveguide.

The acoustical waveguides useful in the present invention are generally made from materials that have an acoustic impedance $Z_1$, that is greater than the acoustic impedance $Z_2$, of the uncured composition and substantially equal to the acoustic impedance $Z_3$, of the cured product. The acoustic impedance (Z) refers to the product of the density of the material through which the sound waves are traveling and the speed with which the sound waves travel through the material. These materials should be capable of being formed into smooth surfaced waveguides having a diameter ranging from about 10 microns to about 10 cm. Examples of these materials include steel, sapphire, quartz, plastic, glass polyester fiberglass, epoxy-fiberglass and the like. The preferred acoustical waveguide is made from the cured composition. This ensures that the acoustical waveguide has an acoustic impedance $Z_1$, that is substantially equal to the acoustic impedance $Z_3$, of the cured product. The use of acoustical waveguides of the cured composition is also desirable because the acoustic impedance of the waveguide is affected by the process conditions in the same manner as the acoustic impedance of the cured product. Therefore, any error in monitoring the curing process attributable to the differing effect of the process conditions on the acoustic impedances is eliminated by using waveguides prepared from the cured composition.

When the optical or acoustical waveguide includes the preferred cured composition, the waveguides can be prepared by forming a puddle of the uncured composition and allowing it to cure to a point where the viscosity of the composition allows it to adhere to a tool and be drawn into a fiber. Alternatively, the waveguide can be prepared by extruding the uncured or partially cured composition through a die that ensures a waveguide with smooth walls. The waveguide can also be made by molding the uncured or partially cured composition in a form that provides a waveguide with a smooth surface. In each method, after the waveguide is formed, it is subjected to curing conditions to provide a waveguide of the cured composition.

Acoustic transducers are used to generate a sound wave in the acoustical waveguide. Generally, two transducers will be used, one at each end of the acoustical waveguide, one for sending the sound and the other for receiving the sound. The transducers work by changing an electrical signal into a sound signal and, in reverse, by changing a sound signal back into an electrical signal. It is also possible to use a single transducer by bouncing the sound wave off one end of the waveguide so that the sending transducer also becomes the receiving transducer. If a sound wave is bounced off the end of the waveguide, it may be desirable to put an acoustically mismatched material on the end of the waveguide to maximize the reflectance of the sound wave back into the waveguide.

Any frequency of sound waves that the acoustical waveguide will transmit may be used, generally ultrasonic sound waves, typically about 10 kilohertz to about 10 megahertz, are used as the transducers at these frequencies are highly developed. Preferably, the frequency of the sound waves is chosen so that the attenuation in the waveguide surrounded by the curing composition is not excessive. If the acoustical waveguide is very short, a higher level of attenuation will be tolerable.

In order for an acoustical waveguide to effectively transmit sound waves, the acoustic impedance $Z_2$, of the medium surrounding the acoustical waveguide must be less than the acoustic impedance $Z_1$, of the acoustical waveguide. The sound waves will be guided by the waveguide in a manner entirely analogous to the guiding of light waves in the optical waveguides. Because of the difference between the acoustic impedance of the uncured composition and the acoustical waveguide at the beginning of the curing process, a fraction of the sound waves introduced into the acoustical waveguide are transmitted by the acoustical waveguide through the curing composition. As the degree of cure increases and the acoustic impedance $Z_2$, of the curing composition increases and approaches the acoustic impedance $Z_1$, of the acoustical waveguide, the intensity of sound waves transmitted by the acoustical waveguide through the curing composition diminishes. The decrease in the intensity of sound waves transmitted by the acoustical waveguide through the curing composition is a result of an increasing intensity of the introduced sound waves escaping the acoustical waveguide. The intensity of sound waves transmitted by the acoustical waveguide can be detected by the ultrasonic transducer positioned on the end of the acoustical waveguide opposite the sound source. The detected intensity of sound waves transmitted by the acoustical waveguide through the curing composition is compared to reference standards to monitor the degree of cure during the curing process.

These reference standards for a given acoustic source provide a relationship between the intensity of detected sound waves transmitted by the acoustical waveguide and the degree of cure during the curing process. The relationships can be established by simultaneously monitoring the degree of cure by an independent means such as differential scanning calorimetry or differential thermal analysis, and relating this information to the intensity of sound waves transmitted by the acoustical waveguide during the curing process.

When the acoustical waveguide is employed, it is possible to determine the complete curing of the resin without referring to the reference standards. Because the acoustical waveguide has an acoustic impedance $Z_1$, substantially equal to the acoustic impedance $Z_3$, of the cured product, when the curing of the resin is complete and the acoustic impedances of the waveguide and curing composition are substantially equal, most of the sound waves will escape the acoustical waveguide and only a minimal intensity of sound waves will be detected as sound waves that have been transmitted through the curing composition. Therefore, the completion of the curing of the resin is indicated by a substantial absence of any detectable intensity of sound waves being transmitted by the acoustical waveguide through the cured product.

The degree of cure can be monitored in any portion of the uncured composition by passing the optical or acoustical waveguide through that particular region of the uncured composition. It is within the scope of the present invention to use more than one optical or acoustical waveguide to monitor the degree of cure in different regions of the curing composition. Because the optical or acoustical waveguides will remain in the cured product when the curing process is completed, the optical or acoustical waveguides are preferably positioned so as not to hinder the strength or function of the cured product.

Referring to FIG. 1, an optical waveguide 10 passes through the curing composition 16. The first end of the optical waveguide 10 is optically coupled to a light source 2 by means of an input fiber 6 that is clad to prevent the escape of light from the input fiber 6. Light that is introduced into the optical waveguide 10 by the input fiber 6 is transmitted by internal reflection through the unclad optical waveguide 10 to its second end where it enters an output fiber 8 that is optically coupled to a photodetector 4. The output fiber 8 is clad in a similar manner as the input fiber 6 to prevent any escape of the transmitted light 12 that enters the output fiber 8 from the optical waveguide 10. The transmission characteristics of the optical waveguide 10 are determined from the transmitted light 12 that is detected by the photodetector 4 and provides information that may be related to reference and control standards to determine the degree of cure in the curing composition 16. As the curing process approaches completion, the amount of light introduced into the optical waveguide 10 from input fiber 6 that escapes within the curing composition (as represented by arrows 14) increases until substantially all of the light that is introduced into the optical waveguide 10 passing through the curing composition 16 escapes within the curing composition 16. This results in a substantial absence of transmitted light 12 being detected by the photodetector 4.

The reference materials that are inserted into the uncured composition to monitor the degree of cure can also be in the form of particles. When used in conjunction with light waves, the index of refraction $n_1$, of the particles should be unequal to the index of refraction $n_2$ of the uncured composition, and substantially equal to the index of refraction $n_3$, of the cured product. When used in conjunction with sound waves, the reference particles should have an acoustic impedance $Z_1$, that is unequal to the acoustic impedance $Z_2$, of the uncured composition and substantially equal to the acoustic impedance $Z_3$, of the cured product. The size of the particles should be as nearly comparable to the wavelength of the optical or acoustical excitation as possible in order to enhance the scattering efficiency of the particles. Generally, when light waves are used, the size of the particles is about 0.1 to about $10\mu$ and preferably, the size ranges from about 0.5 to about $2\mu$. When sound waves are used, the wavelength of the acoustic excitation varies over four orders of magnitude, therefore, the size of the reference particles can vary over a wide range, with the prime concern being the effect of the particle size on the curing process and the properties of the cured product. In order to ensure that the particles have an index of refraction or acoustic impedance substantially equal to the cured product, it is preferred that the particles be prepared from the cured composition. The use of reference particles of the cured composition is desirable because, as discussed, the index of refraction or acoustic impedance of the particles is affected by the process conditions in the same manner as the index of refraction or acoustic impedance of the cured product. Therefore, any error in monitoring the degree of cure attributable to the differing effect of the process conditions on the indices of refraction or acoustic impedances is eliminated by using reference particles prepared from the cured composition. If the particles are produced from a material other than the cured composition, the material should be such that the particles do not adversely affect the properties, such as strength, adhesion, flexibility and the like or the function of the cured product.

Prior to subjecting the uncured composition to curing conditions, the particles are uniformly dispersed throughout the uncured composition in an amount ranging from about 0.001 to about 10 percent. When using the particles, the degree of cure in the curing process is determined by relying on the difference between the index of refraction or the acoustic impedance of the reference particles and the curing composition in a manner similar to that discussed with regard to the waveguides. The particles, rather than waveguides are used as a reference material against which the index of refraction or acoustic impedance of the curing composition is indirectly compared by monitoring the scattering or reflection of light or acoustic waves by the particles within the curing composition.

Specifically, when light waves are used in conjunction with the reference particles to monitor the degree of cure, light can be introduced from the exterior of the curing composition, for example, by a laser beam or to the interior of the curing composition by an optical fiber terminated within the curing composition. When the particles are employed as the reference material, the absorption of light that is introduced into the curing composition should be minimal to ensure the detectability of the scattered light. The introduced light will generally have a wavelength of about 0.4 to about 10 microns. Because of the difference between the index of refraction of the particles and the curing composition, the light that is introduced into the curing composition, internally or externally, will be reflected and scattered by the particles. The reflected and scattered light will be readily detectable with photodetectors that transforms the light signal into an electrical signal. Because the scattering and reflecting of the light introduced into the curing composition is dependent upon the difference between the index of refraction of the particles and the curing composition, as the degree of cure increases and this difference decreases, the amount of reflected and scattered light will decrease. That is, as the index of refraction of the particles and the curing composition approach each other, the curing composition becomes a homogeneous optical medium through which the light will pass without being reflected and scattered. When the resin is completely cured, the index of refraction of the particles and the cured composition are substantially equal to each other and therefore, the light that is introduced into the cured composition is no longer reflected or scattered by the particles and passes through the cured product.

The light that is reflected and scattered by the particles can be monitored from the exterior of the curing composition by conventional means such as the unaided eye if the light is in the visible range or a photodetector. The reflected and scattered light in a particular region of the curing composition can be guided from the interior of the curing composition to a photodetector by terminating an optical waveguide within the curing composition. The reflected and scattered light that is detected by the detection means can be compared to predetermined reference standards to determine the degree of cure. The reference standards for a given light source provide a relationship between the intensity of light reflected and scattered and the degree of cure. The reference standards can be obtained as discussed hereinbefore with regard to the optical waveguides.

As with the optical waveguides, detecting the completion of the curing of the resin does not require a comparison to the reference standards. The index of refraction of the particles and the curing composition become substantially equal as the degree of cure approaches completion, and therefore the reflection and scattering of the light that is introduced into the curing composition diminishes. As a consequence, the completion of the curing of the resin is evidenced by a substantial absence of any detectable intensity of light being scattered or reflected within the cured product.

The reference particles can also be used in conjunction with acoustic waves to monitor the degree of cure in a curing process. When the acoustic waves are used to monitor the degree of cure, the acoustic impedance $Z_1$, of the reference particles is substantially equal to the acoustic impedance $Z_3$, of the cured product. The particles are dispersed throughout the uncured composition in the same manner and in the same amount as discussed with regard to the dispersing of the particles used when light waves are used to monitor the curing process.

The acoustic waves are introduced to the interior of the curing composition using an acoustical waveguide or to the exterior of the curing composition by attaching an acoustical waveguide to the surface of the curing composition. The acoustic waves introduced into the curing composition containing the particles has a frequency of about 10 kHz to about 10 MHz.

Because of the difference between the acoustic impedance of the reference particles and the curing composition, the acoustic waves will be reflected and scattered by the particles in much the same manner as the light waves are reflected and scattered by the particles. The reflection and scattering will continue until the acoustic impedance of the curing composition becomes substantially equal to the acoustic impedance of the particles. As with the light waves and the index of refraction, the scattering of the acoustic waves provides an indirect measure of the difference between the acoustic impedance of the particles and the acoustic impedance of the curing composition. The reflection and scattering of the acoustic waves can be monitored from the exterior of the curing composition by conventional means such as pulsed acoustic transmission and range gated receivers. The reflected and scattered acoustic waves may also be detected from the interior of the curing composition using acoustical waveguides for receiving and transmitting acoustic waves to an acoustic detector such as an acoustic transducer. The intensity of scattered acoustic waves that is detected is compared to reference standards for a given sound source to monitor the degree of cure in the curing process. The reference standards provide a relationship between the detected intensity of acoustic waves that is scattered and reflected by the particles and the degree of cure in the curing composition. These reference standards are established by means described hereinbefore with regard to the optical and acoustical waveguides.

In order to determine the completion of the curing of the resin using sound waves and the reference particles, it is not necessary to refer to the reference standards. Because the acoustic impedance of the particles and the acoustic impedance of the cured product are substantially equal, the completion of the curing of the resin is indicated by a substantial absence of any detectable intensity of reflected and scattered acoustic waves.

When using the particles as the reference material, the cured product should be substantially free of intrinsic inhomogeneities such as bubbles in the cured product or extraneous foreign materials that would cause background scattering. If it is desired to monitor the curing of compositions including reinforcing fibers or other materials which render the curing composition optically or acoustically inhomogeneous, it is preferred that the methods using optical or acoustical waveguides be used, since detection of the transmission characteristics of the waveguides, unlike the detection of the intensity of scattered waves is substantially unaffected by the discontinuities in the curing composition. If reference particles are used in conjunction with a curing composition which is optically or acoustically inhomogeneous, the scattering of light or acoustic waves from the inhomogeneity of the curing composition may be larger than the scattering from the reference particles, and therefore the scattering from the reference particles will not be measurable with sufficient accuracy to provide a means for monitoring the curing of the composition.

Figure 2:
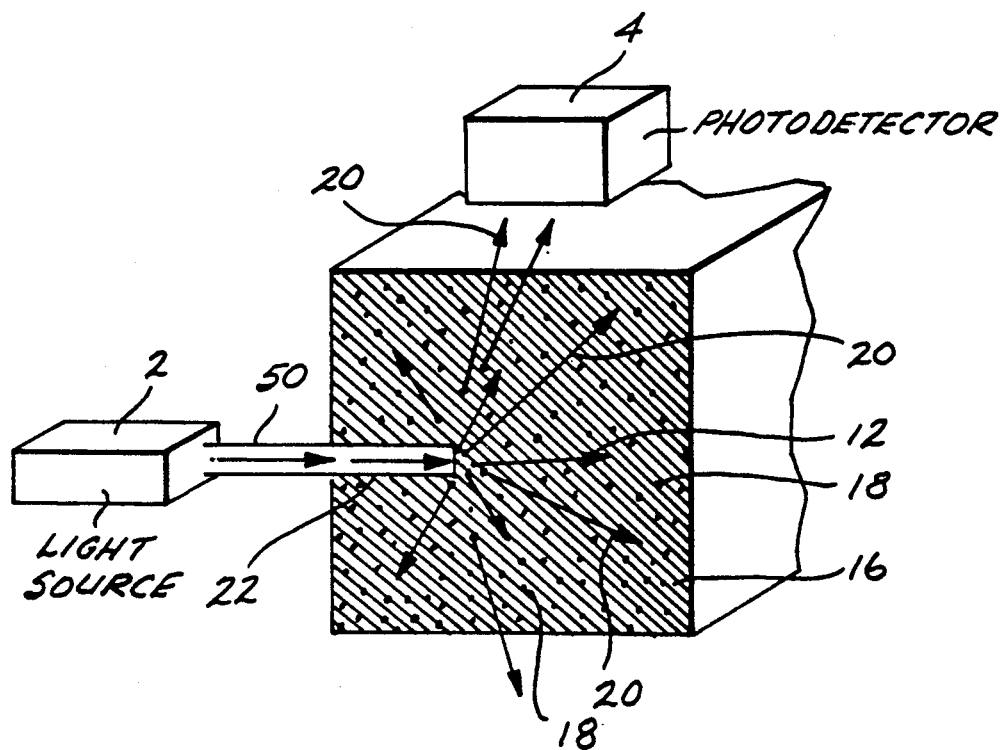
FIG. 2 is a schematic diagram of a second apparatus constructed in accordance with the present invention.

Referring to FIG. 2, the numbering in FIG. 1 has been adopted for those items in FIG. 2 that are consistent with the items in FIG. 1. Reference particles 18 are dispersed throughout the curing composition 16. Light from light source 2 is introduced into the optical waveguide 22 through input fiber 50. The input fiber 50 is preferably clad to prevent escape of light therefrom prior to entering the optical waveguide 22. The optical waveguide 22 is terminated within the curing composition so that light may be introduced to the interior of the curing composition 16.

Light that is introduced into the interior of the curing composition 16 is reflected by the particles 18 (as represented by arrows 20) and is detected by photodetector 4. As the curing process approaches completion, and the index of refraction of the particles 18 and the curing composition 16 approach each other, the intensity of the scattered light waves 20 decreases and substantially all of the introduced light is transmitted (as indicated by arrow 12) through the curing composition 16. The intensity of the scattered light waves 20 that is detected by the photodetector 4 can be related to reference and control standards to provide an indication of the degree of cure in the curing composition 16.

Another method for monitoring the degree of cure that takes advantage of the reflective properties of an interface between two materials having a different index of refraction employs a transparent ellipsoidal-shaped sensor of a material that has an index of refraction $n_1$, that is unequal to the index of refraction $n_2$, of the curing composition and substantially equal to the index of refraction $n_3$, of the cured product. Preferably, the ellipsoidal sensor structure is prepared from the uncured composition in a cured form. The use of an ellipsoidal sensor structure prepared from the cured composition is desirable because the index of refraction of the sensor structure is affected by the process conditions in the same manner as the index of refraction of the cured product. Therefore, any error in monitoring the degree of cure attributable to the differing effect of the process conditions on the indices of refraction is eliminated. If the ellipsoidal sensor is prepared from a material other than the cured composition, the material should be of the type that does not adversely affect the properties or function of the cured product and is not adversely affected by the curing conditions.

Figure 3:
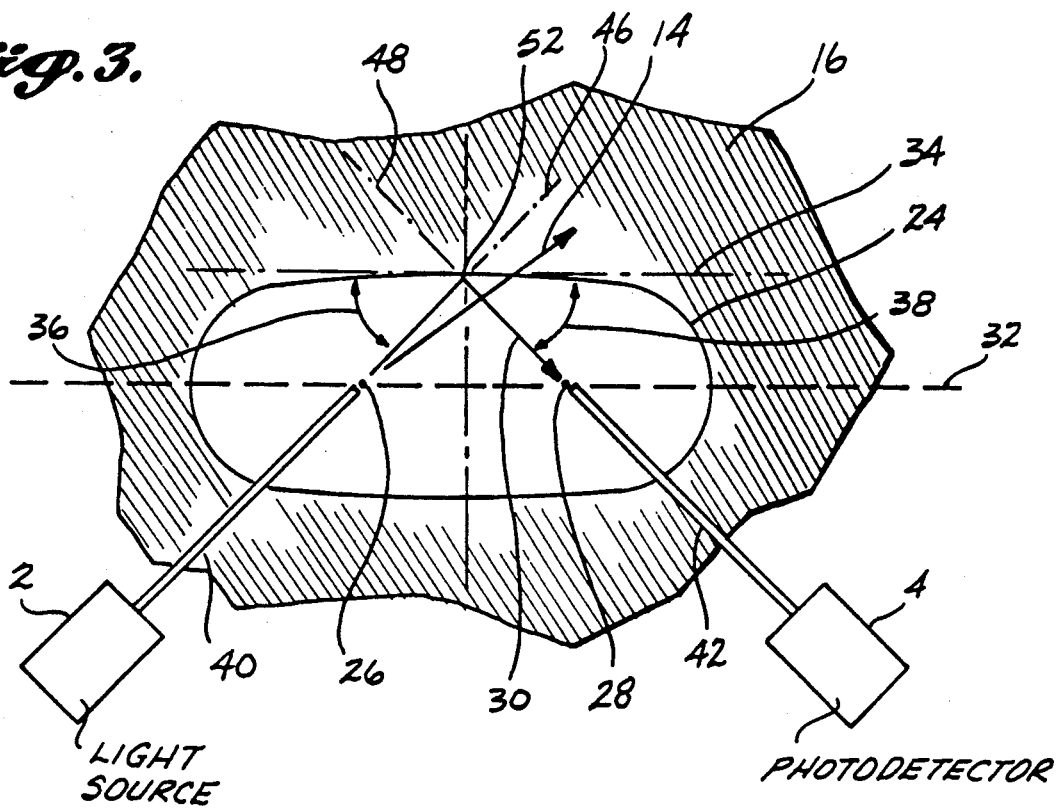
FIG. 3 is a schematic diagram of a third apparatus in accordance with the present invention.

Referring to FIG. 3, the numbering in FIGS. 1 and 2 has been adopted in FIG. 3 for those items in FIG. 3 that are consistent with the items in FIGS. 1 and 2. An ellipsoidal sensor 24 having a first optical waveguide 40 and a second optical waveguide 42 terminated at the first focus 26 and the second focus 28 respectively, is surrounded by a curing composition 16. The longitudinal axes 46 and 48 of the waveguides 40 and 42 at their termination within the ellipsoidal sensor structure 24 and the major axis 32 of the ellipsoidal sensor structure 24 are preferably coplanar. In addition, the first 40 and second 42 optical waveguides are preferably arranged so that light may not pass directly from one waveguide 40 to the other waveguide 42, but instead the light emanating from the end of the first optical waveguide 40 and reflected from the surface of the ellipsoidal sensor structure 24 would optimally enter and be guided in the second waveguide 42. Because of the difference between the index of refraction of the ellipsoidal sensor 24 and the curing composition 16 and the known principle that rays originating from one focus of an ellipsoid will be reflected by the boundary of the ellipsoid to the second focus, a portion of the light that is introduced into the sensor structure 24 at one focus 26 by the first optical waveguide 40 coupled to the light source 2 is reflected back to the second focus 28 of the ellipsoidal sensor 24. A fraction of the reflected light 30 is guided out from the sensor structure 24 by the second optical waveguide 42 that is terminated at the second focus 28, and detected by conventional means, such as a photocell 4. Preferably, in order to detect as much of the reflected light 30 as possible, the first 40 and second 42 optical waveguides should be positioned at the first 26 and second 28 focus respectively, so that the extensions of their longitudinal axes 46 and 48 beyond their terminations at the foci 26 and 28, intersect the boundary of the ellipsoidal sensor structure 24 at the same point 52, and the tangent 34 to the boundary at this point 52 in the plane of the longitudinal axes 46 and 48, forms equal angles 36 and 38 with the extensions of the longitudinal axis 46 of the first optical waveguide 40 and the longitudinal axis 48 of the second optical waveguide 42.

The intensity of reflected light 30 that is guided by the second optical waveguide 42 and detected by the photodetector 4 is compared to reference standards for a given light source 2 similar to those described hereinbefore, to determine the degree of cure in the curing composition 16. As the curing of the resin approaches completion, the difference between the index of refraction of the ellipsoidal sensor 24 and the curing composition 16 decreases until the indices of refraction are substantially equal. When the indices of refraction are substantially equal, the intensity of light 30 reflected by the boundary of the sensor 24 back to the second focus 28 decreases because most of the light escapes the sensor (indicated by arrow 14). The completion of the curing of the resin is indicated by a substantial absence of any detectable intensity of light being reflected back to the second focus 28. Therefore, when it is desirable to only determine the completion of the curing of the resin rather than monitor the curing process, comparison of the intensity of detected light to the reference standards is not necessary.

The frequency and wavelength of the light introduced into the ellipsoidal sensor structure may vary over the same ranges referred to with regard to the optical waveguides and reference particles. Where the ellipsoidal sensor is used to monitor the degree of cure in the curing composition, and the curing composition contains other materials that will reflect light, such as plies of reinforcing fibers, the intensity of light reflected back to the focus by these materials should be minimized in order to ensure accuracy of the measurement. For example, when reinforcing fibers are employed, the reflection of light by the reinforcing fibers is minimized by using light having a wavelength that is highly absorbed by the curing composition and the cured product. The absorption of the light results in the range of propagation of the light being smaller than the distance between adjacent plies of the reinforcing fibers, therefore reducing the potential for the undesired reflection.

It is to be understood that modifications and changes to the preferred embodiment of the invention herein described and shown can be made without departing from the spirit and scope of the invention. The following examples are set forth to illustrate the present invention. They are not, however, to be considered as limitations thereof.

EXAMPLE

An optical waveguide one (1) cm in length and tapered from 1 mm to about 0.5 mm in diameter is fabricated from DEVCON ® 5-Minute ® Epoxy, available from Devcon Corp., Danvers, Mass., by drawing a fiber from a pool of the partially cured epoxy resin and permitting the fiber to cure. The fiber has a gentle S-bend shape, similar to an integral sign. Each end of the fiber is epoxied to a 600 $\mu$core step index plastic fiber available from Poly-Optical Products, Inc., Santa Ana, Calif. The input plastic fiber attached to the 1 mm diameter end of the epoxy fiber is illuminated with a GaAs laser, available from General Optronics, Edison, N.J., and the output plastic fiber attached to the 0.5 mm diameter end of the epoxy fiber directs the transmitted light to a silicon photodetector, available from United Detector Technology, Hawthorne, Calif. Reference is made to FIG. 1 for a schematic illustration of the apparatus.

The GaAs laser was modulated at 1000 Hz, and the output of the silicon cell is detected using a lock-in amplifier to remove any effect from ambient lighting. In air, the epoxy resin fiber transmits light with a detectable signal of 470 relative units.

Figure 4:
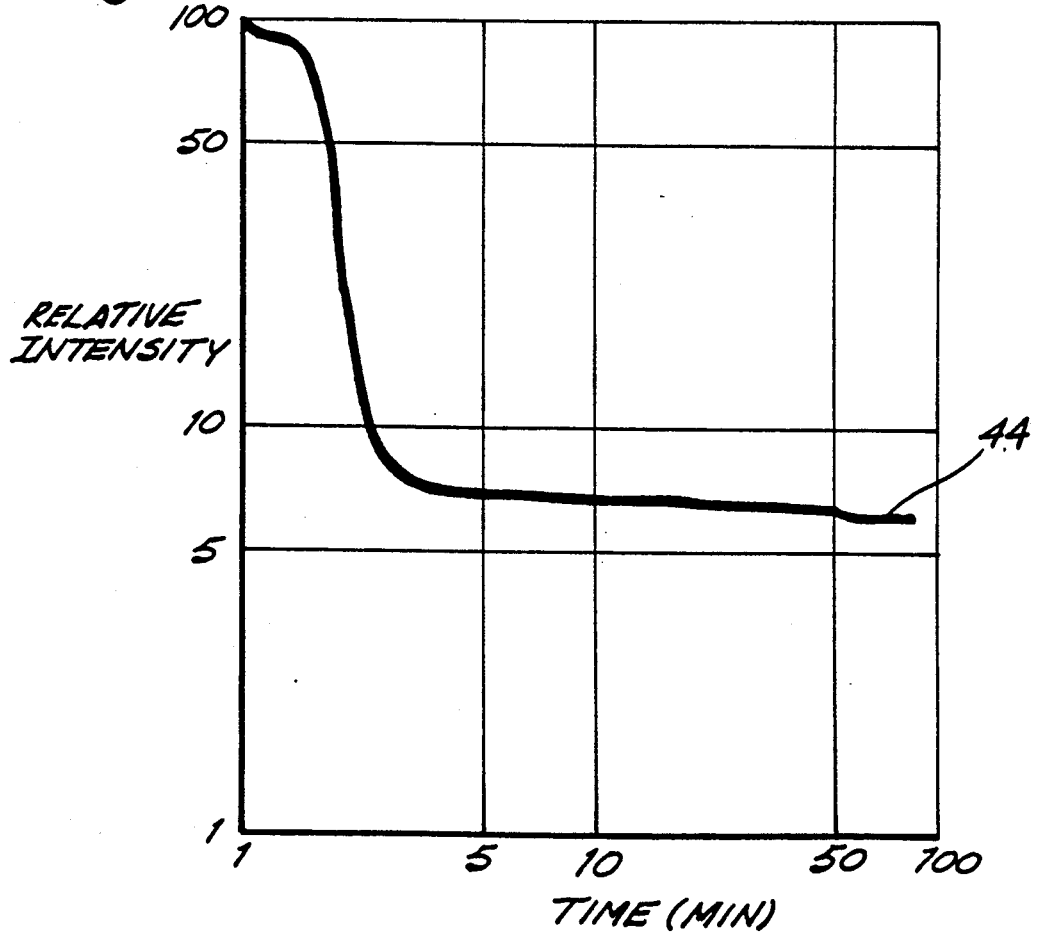
FIG. 4 is a graph illustrating the relationship between the curing process and the intensity of transmitted light in accordance with a preferred embodiment illustrated in FIG. 1.

The epoxy resin fiber is then immersed in a freshly mixed pool of the 5-Minute ® Epoxy. The detected signal level immediately falls to 90 relative units and as the pool of 5-Minute ® Epoxy is cured under ambient conditions, the detected signal decreases and falls to six relative units after about 5 minutes. The relationship between the degree of cure as a function of time (X-axis) and the intensity of transmitted light (Y-axis) is illustrated in FIG. 4 by line 44. Referring to FIG. 4, as the degree of cure increases with time, the intensity of the light decreases from 90 relative units to about 6 relative units, this decrease in transmitted light provides adequate resolution, to accurately monitor the final stages of the curing process using the method in accordance with the present invention.

Particular embodiments of the present invention described above are to be considered in all respects as illustrative and not restrictive. The scope of Letters Patent granted thereon is to be limited only by the definition set forth in the appended claims and equivalents thereof.

The embodiments of the invention in which an exclusive property or privilege is claimed are defined as follows:

1. A method of monitoring a process wherein a liquid composition passes from a liquid phase to a solid phase comprising the steps:

(a) dispersing particles having an acoustic impedance $Z_1$ in the liquid composition having an acoustic impedance $Z_2$, such that $Z_1$ and $Z_2$ are unequal, the solid phase of the liquid composition having an acoustic impedance $Z_3$ that is substantially equal to $Z_1$;

(b) providing a solidifying composition by subjecting the liquid composition containing the particles to conditions that cause the liquid composition to solidify;

(c) introducing acoustic waves into the solidifying composition containing the particles; and (d) detecting the introduced acoustic waves scattered by the particles.

2. The method of claim 1, further comprising:

(e) comparing the acoustic waves detected in step (d) with reference standards to determine the degree of solidification of the liquid composition.

3. The method of claim 1, wherein the particles include the liquid composition in a solid phase.

4. The method of claim 1, wherein step (d) comprises:

(d) detecting the introduced acoustic waves scattered by the particles, the intensity of the introduced acoustic waves scattered by the particles decreasing as the degree of solidification increases.

5. The method of claim 1, wherein step (d) comprises:

(d) detecting the introduced acoustic waves scattered by the particles, the completion of the solidification of the liquid composition being indicated by a substantial absence of scattering of the introduced acoustic waves by the particles.

6. The method of claim 1, wherein the liquid composition is a thermosettable resin composition.

7. A method of monitoring a process wherein a liquid composition passes from a liquid phase to a solid phase comprising the steps:

(a) passing an acoustical waveguide having an acoustic impedance $Z_1$ and including the liquid composition in a solid phase through the liquid composition having an acoustic impedance $Z_2$, such that $Z_2$ is less than $Z_1$, the solid phase of the liquid composition having an acoustic impedance $Z_3$, such that $Z_3$ substantially equals $Z_1$;

(b) subjecting the liquid composition containing the acoustical waveguide to conditions that cause the liquid composition to solidify;

(c) transmitting acoustic waves through the acoustical waveguide; and (d) detecting the intensity of acoustic waves transmitted through the portion of the acoustical waveguide passing through the solidifying composition, the intensity of acoustic waves transmitted through the acoustical waveguide decreasing as the degree of solidification increases, completion of the solidification of the liquid composition being indicated by a substantial absence of any detectable intensity of acoustic waves being transmitted by the acoustical waveguide through the solidifying composition.

8. The method of claim 7, further comprising the step:

(e) comparing the intensity of acoustic waves detected in step (d) with reference standards to determine the degree of solidification of the liquid composition.

* * * * *

UNITED STATES PATENT AND TRADEMARK OFFICE
CERTIFICATE OF CORRECTION

PATENT NO. : 5,009,102

DATED : April 23, 1991

INVENTOR(S) : M. A. Afromowitz

It is certified that error appears in the above-identified patent and that said Letters Patent is hereby corrected as shown below:

| Column | Line | |
|---|---|---|
| (57) Abstract | 9 | "in situ" should be --*in situ*-- |
| 1 | 49 | "in situ" should be --*in situ*-- |
| 1 | 53-54 | "in situ" should be --*in situ*-- |
| 2 | 31 | "in situ" should be --*in situ*-- |
| 2 | 37 | "in situ"should be --*in situ*-- |
| 6 | 3 | "difference"should be --*difference*-- |

Signed and Sealed this

Twenty-eighth Day of April, 1992

Attest:

HARRY F. MANBECK, JR.

*Attesting Officer*     *Commissioner of Patents and Trademarks*